(12) United States Patent
Nelson

(10) Patent No.: US 6,756,354 B2
(45) Date of Patent: Jun. 29, 2004

(54) THERAPEUTIC COMPOSITIONS CONTAINING OLIGO (ETHYLENE GLYCOL)-TERMINATED 1,2-DITHIOLANES AND THEIR CONJUGATES

(76) Inventor: Deanna Jean Nelson, 104 Tasman Ct., Cary, NC (US) 27513

( * ) Notice: Subject to any disclaimer, the term of this patent is extended or adjusted under 35 U.S.C. 154(b) by 0 days.

(21) Appl. No.: 10/115,558

(22) Filed: Apr. 3, 2002

(65) Prior Publication Data

US 2003/0044402 A1 Mar. 6, 2003

Related U.S. Application Data

(63) Continuation-in-part of application No. 09/946,023, filed on Sep. 5, 2001.

(51) Int. Cl.[7] .................. A61K 38/00; C12N 11/08; G01N 33/545; C07K 17/08; C07K 17/14
(52) U.S. Cl. .................. 514/2; 424/450; 435/176; 435/180; 436/525; 436/531; 530/420; 530/811; 530/815
(58) Field of Search ................. 435/174, 177, 435/180; 530/402, 810, 812, 815, 811; 436/518, 524, 531, 525; 424/400, 450; 514/2

(56) References Cited

U.S. PATENT DOCUMENTS 5,906,977 A * 5/1999 Sinn et al. .................. 514/12
6,492,560 B2 * 12/2002 Wilbur et al. ............... 564/505

FOREIGN PATENT DOCUMENTS

WO     WO 99/14596    * 3/1999

OTHER PUBLICATIONS

Bandyopadhyay et al., chem. Commun., 2000, pp. 141–142.*

* cited by examiner

Primary Examiner—David M. Naff
(74) Attorney, Agent, or Firm—Deanna J. Nelson

(57) ABSTRACT

The present invention provides biotechnologically useful oligo(ethylene glycol)-terminated 1,2-dithiolane compositions and conjugates of these compositions with biological or non-biological receptor, ligand, sequestering, or reporter moieties to provide physiologically active therapeutic compositions. The invention also provides methods for the preparation of these compositions. Further, the invention provides self-assembled monolayer (SAM) compositions on a metal and methods for their preparation.

17 Claims, 1 Drawing Sheet

THERAPEUTIC COMPOSITIONS CONTAINING OLIGO (ETHYLENE GLYCOL)-TERMINATED 1,2-DITHIOLANES AND THEIR CONJUGATES

CROSS-REFERENCE TO RELATED APPLICATIONS

This application is a continuation-in-part of U.S. patent application Ser. No. 09/946,023, filed Sep. 5, 2001.

STATEMENT REGARDING FEDERALLY SPONSORED RESEARCH & DEVELOPMENT

No Federally sponsored research and development were used in making this invention.

BACKGROUND OF THE INVENTION

Since they were first reported by Nuzzo and Allara in 1983, self-assembled monolayers (SAMs) composed of sulfur-terminated organic molecules adsorbed on and adherent to gold surfaces have shown broad utility in lubrication, electrochemistry, electronic and vibrational spectroscopy, photochemistry, diagnostics, the modification of biochemical membranes, catalysis, drug delivery, and facile modification of the absorptive properties of surfaces. (R. G. Nuzzo and D. L. Allara. Adsorption of bifunctional organic disulfides on gold surfaces. J. Am. Chem. Soc. 1983; 105: 4481–4483.) More recently, organic modifications of gold surfaces by SAMs have proven to be successful in nanotechnological biosensor applications, e.g., in commercially available chips for biomolecular interaction analysis with surface plasmon resonance. (S. Löffås, B. Johnsson, K. Tegendahl, and I. Rönnberg. Colloids Surf. B 1993; 1: 83–89.) For example, Dijksma and coworkers have reported that an electrochemical immunosensor composed of self-assembled monolayers of cysteine or N-acetylcysteine on gold electrodes is useful for the detection of interferon-γ at the attomolar level. (M. Dijksma, B. Kamp, J. C. Hoogvliet, and W. P. van Bennekom. Development of an electrochemical immunosensor for direct detection of interferon-γ at the attomolar level. Analyt. Chem. 2001; 73: 901–907.) Similarly, Darder and coworkers have found that horseradish peroxidase retained its activity when immobilized onto a gold surface via a 3-thiopropionate tether and was useful as a peroxide biosensor. (M. Darder, K. Takeda, F. Pariente, E. Lorenzo, and H. D. Abruña. Dithiobissuccinimidyl propionate as an anchor for assembling peroxidases at electrodes surfaces and its application in a $H_2O_2$ biosensor. Analyt. Chem. 1999; 71: 5530–5537.)

Likewise, poly- and oligo(ethylene glycols) (PEGs or OEGs, respectively; Structure 1, where $R_1$ is MeO or HO and $R_2$ is OH) have found widespread use in a variety of biotechnological and commercial applications, including the preparation of surfactants, ion-conducting materials, and conjugates of low and high molecular weight molecules. Investigators have found that these glycols provide good anchors for biological and non-biological receptor/reporter molecules or for ligands for biological and non-biological chelation or binding sites. Moreover, both PEGs and OEGs are known to reduce the nonspecific binding of proteins and other bioactive molecules to the surface to which they are conjugated. PEG and OEG derivatives are ideal for these applications because they are inexpensive, water soluble, stable, nonantigenic and non-immunogenic, and commercially available in a wide range of molecular weight distributions.

Structure 1: $R_1$—$CH_2CH_2O$—$(CH_2CH_2O)_x$—$CH_2CH_2$—$R_2$

In addition, conjugation with more highly branched and dendritic poly- and oligo(ethylene glycols) has been reported to be useful for improving the stability of protein drugs. [(a) D.C. Tully and J. M. J. Frechet. Dendrimers at surfaces and interfaces: chemistry and applications. Chem. Commun. 2001; 1229–1239. (b) I. Fuke, T. Hayashi, Y. Tabata, and Y. Ikada. Synthesis of poly(ethylene glycol) derivatives with different branchings and their use for protein modification. J. Controlled Release 1994; 30: 27–34. (c) J. M. Harris, F. M. Veronese, P. Caliceti, and O. Schiavon, U.S. Pat. No. 5,932,462.]

The broad utility of both classes of reagents (i.e., SAMs and PEGs or OEGs) suggests that synergistic benefits would obtain if libraries of reagents were available that combined the beneficial attributes of a SAM with those a PEG or OEG and exhibited additional features, such as the presence of reactive or activated groups at one end of each PEG or OEG chain. This combination of attributes would enable attachment of one terminus of such a combined SAM-forming-OEG reagent to a metal surface, yielding a SAM-OEG reagent, and attachment of a biological or non-biological receptor, ligand or reporter moiety at each of the other activated or reactive termini of the combined SAM/OEG reagent. The literature reports that describe examples of combined SAM/OEG reagents are limited to disclosures of methods of synthesis of OEG conjugates of linear alkyl monothiols and the effects of structure on the stability and physico-chemical properties of the reagents and the SAMs formed from them. (S. Svedhem, C-A. Hollander, J. Shi, P. Konradsson, B. Liedberg, and S. C. T. Svensson. Synthesis of a series of oligo(ethylene glycol)-terminated alkanethiol amides designed to address structure and stability of biosensing surfaces. J. Org. Chem. 2001; 66: 4494–4503.) Thus, the known reagents are limited to alkyl monothiols that lack an activated or reactive terminus at the end of the OEG chain and other desirable attributes that would enhance their utility.

Clearly, significant biotechnological advances in a spectrum of areas would be possible if activated or reactive, oligo(ethylene glycol)-terminated reagents and OEG-terminated reagents conjugated with a biological or non-biological receptor, ligand or reporter moiety useful for preparing self-assembled monolayers on gold were available. The present invention addresses this need.

Moreover, significant therapeutic benefit would result if the pharmaceutical or pharmacological properties of a therapeutic agent were enhanced by conjugatively coupling with oligo(ethylene glycol)-terminated dithiolane reagents and OEG-terminated dithiolane reagents.

SUMMARY OF THE INVENTION

The invention is based upon the recognition that the availability of activated or reactive, oligo(ethylene glycol)-terminated dithiolane compositions suitable for use in preparing self-assembled monolayers on a metal would enable significant advances in the biotechnological arts.

Thus, the invention provides highly versatile tethers suitable for immobilization on a metal backbone, wherein one segment of the tether is a linear or branched oligo(ethylene glycol) residue and the other segment of the tether is an alkyl-substituted 1,2-dithiolane. Further, one terminus of each oligo(ethylene glycol) residue is activated or reactive, enabling the preparation of conjugates of the oligo(ethylene glycol)-terminated dithiolane compositions that are also suitable for immobilization on a metal backbone.

One embodiment of the present invention comprises linear or branched oligo(ethylene glycol)-terminated 3-alkyl-1,2-dithiolanes having the formula:

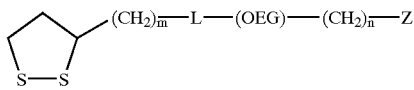

wherein m is from about 3 to about 20; n is from 2 to about 6; OEG is shorthand for a linear oligoether having the general structure —$(CH_2CH_2O)_x$— wherein x is from 2 to about 100, or for a branched oligoether wherein each branch comprises a linear oligoether having this general structure; one terminus of the OEG residue is covalently joined to the terminus of the alkyl side chain of the dithiolane by a linker L, wherein L is N, O, S, P, or an amide or hydrazide group; and each of the other termini of the OEG residue is a reactive or activated substituent Z that can be joined covalently to a biological or non-biological, ligand, sequestering, or reporter moiety. Examples of suitable reactive or activated substituents Z include an amino, guanidino, sulfhydryl, or activated ester moiety; a substituent that is reactive toward nucleophilic displacement, such as chloride, bromide, iodide, tosylate, tresylate, or mesylate; a group that is reactive toward nucleophilic addition, such as cyanate, isocyanate, thiocyanate, isothiocyanate, maleimide, oxirane, thiirane, or azirane; a carbonyl group; or a hydroxyl group.

A preferred embodiment comprises oligo(ethylene glycol)-terminated thioctic acid derivatives having the formula:

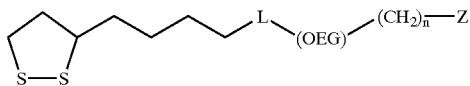

wherein n is from 2 to about 6; the symbol OEG is a linear oligoether having the general structure —$(OCH_2CH_2)_x$— and x is from 2 to about 100, or is a branched oligoether wherein each branch comprises a linear oligoether having this general structure; one terminus of the OEG residue is covalently joined to the alkyl side chain of thioctic acid by a linker L, wherein L is amide or hydrazide; and each of the other termini of the OEG residue is a reactive or activated substituent Z that can be joined covalently to a biological or non-biological ligand or reporter moiety.

A particularly preferred embodiment comprises oligo (ethylene glycol)-terminated d-thioctic acid derivatives having the formula:

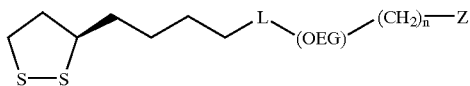

wherein n is from 2 to about 6; the symbol OEG is a linear oligoether having the structure —$(OCH_2CH_2)_x$— and x is from 2 to about 100, or is a branched oligoether wherein each branch comprises a linear oligoether having this structure; one terminus of the OEG residue is covalently joined to the alkyl side chain of d-thioctic acid by a linker L, wherein L is amide or hydrazide; and each of the other termini of the OEG residue is a reactive or activated substituent Z that can be joined covalently to a biological or non-biological ligand or reporter moiety.

Another embodiment of the present invention comprises oligo(ethylene glycol)-terminated 4-alkyl-1,2-dithiolanes having the formula:

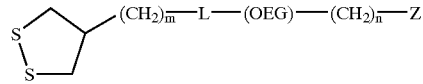

wherein m is from 3 to about 20; n is from 2 to about 6; the symbol OEG is a linear oligoether having the structure —$(OCH_2CH_2)_x$— and x is from 2 to about 100, or is a branched oligoether wherein each branch comprises a linear oligoether having this structure; one terminus of the OEG residue is covalently joined to the terminus of the alkyl side chain of the dithiolane by a linker L, wherein L is N, O, S, P, or an amide, or hydrazide; and each of the other termini of the OEG residue is a reactive or activated substituent Z that can be joined covalently to a biological or non-biological ligand or reporter moiety. Examples of suitable reactive or activated substituents Z include an amino, guanidino, sulfhydryl, or activated ester moiety; a substituent that is reactive toward nucleophilic displacement, such as chloride, bromide, iodide, tosylate, tresylate, or mesylate; a group that is reactive toward nucleophilic addition, such as cyanate, isocyanate, thiocyanate, isothiocyante, maleimide, oxirane, thiirane, or azirane; a carbonyl group; or a hydroxyl group.

Also provided in accordance with the invention are conjugates of these activated polymers with a biological or non-biological receptor, ligand, sequestering, or reporter moiety such as a polypeptide, protein, enzyme, phospholipid, lipid, liposome, nucleoside, oligonucleotide, drug, dye, antibody reporter molecule, ligand, cyclodextrin, carceplex, boronate, biological membrane, or a surface of a solid material that is compatible with living organisms, tissue, or fluids. Further provided are methods for preparation of these conjugates.

Yet another particularly preferred embodiment comprises a conjugatively coupled oligomer composition comprising an oligo(ethylene glycol)-terminated thioctic acid derivative having the formula:

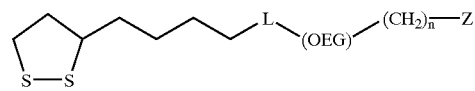

wherein n is from 2 to about 6; the symbol OEG is a linear oligoether having the structure —$(OCH_2CH_2)_x$— and x is from 2 to about 100, or is a branched oligoether wherein each branch comprises a linear oligoether having this structure; one terminus of the OEG residue is covalently joined to the terminus of the alkyl side chain of the dithiolane by a linker L, wherein L is N, O, S, P, or an amide, or hydrazide; and each of the other termini of the OEG residue of the conjugatively coupled oligomer composition is stabilizingly and covalently coupled to a therapeutic agent such as a drug, active pharmaceutical agent, polypeptide, protein, enzyme, phospholipid, nucleoside, oligonucleotide, or antibody, said composition having the capability of interacting with a membrane. The thioctic acid portion of the conjugatively coupled oligomer composition may be racemic or may be enriched in one or the other of the two enantiomeric forms of thioctic acid.

In one particular aspect, the present invention relates to a physiologically active therapeutic agent composition comprising a physiologically active therapeutic agent covalently coupled with an oligo(ethylene glycol)-terminated thioctic acid derivative having the formula:

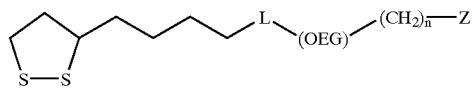

wherein n is from 2 to about 6; the symbol OEG is a linear oligoether having the structure —(OCH$_2$CH$_2$)$_x$— and x is from 2 to about 100, or is a branched oligoether wherein each branch comprises a linear oligoether having this structure; one terminus of the OEG residue is covalently joined to the terminus of the alkyl side chain of the dithiolane by a linker L, wherein L is N, O, S, P, or an amide, or hydrazide; and each of the other termini of the OEG residue of the conjugatively coupled oligomer composition is stabilizingly and covalently coupled to a therapeutic agent such as a drug, active pharmaceutical agent, polypeptide, protein, enzyme, phospholipid, nucleoside, oligonucleotide, or antibody, wherein the oligo(ethylene glycol)-terminated thioctic acid derivative moiety and the physiologically active therapeutic agent are conformationally arranged in relation to one another such that the physiologically active therapeutic agent in the physiologically active therapeutic agent composition has an enhanced in vivo resistance to enzymatic modification or degradation, relative to the physiologically active therapeutic agent alone (i.e., in an unconjugated form devoid of the oligo(ethylene glycol)-terminated thioctic acid derivative moiety coupled thereto).

The invention relates in a further aspect to a stable, conjugated therapeutic agent composition comprising a physiologically active therapeutic agent covalently coupled to a physiologically compatible oligo(ethylene glycol)-modified 1,2-dithiolane moiety. In such composition, the physiologically active therapeutic agent may be covalently coupled to the physiologically compatible oligo(ethylene glycol)-modified 1,2-dithiolane moiety by a labile covalent bond, wherein the labile covalent bond is scissionable in vivo by biochemical hydrolysis and/or proteolysis. The physiologically compatible oligo(ethylene glycol)-modified 1,2-dithiolane moiety may advantageously comprise a physiologically compatible oligo(ethylene glycol)-modified lipoic acid ester or amide.

In the above complex, the physiologically active therapeutic agent may, by way of illustration, comprise a peptide, protein, nucleoside, nucleotide, antineoplastic agent, antiviral agent, anti-resorptive agent, anti-osteoporotic agent, or prodrugs, precursors, intermediates, analogues, or derivatives thereof.

For example, the therapeutic peptide may comprise a peptide selected from the group consisting of insulin, calcitonin, interferons, enkephalins, endorphins, vasopressin, non-naturally occurring opioids, superoxide dismutase, asparaginase, arginase, arginine deaminase, adenosine deaminase, or erythropoietin. The peptide may be human, recombinant, or animal in origin and is obtained and purified by known techniques.

As other examples, the therapeutic agent may comprise an antiviral compound; a cancer chemotherapeutic agent; an antidepressant; an ulcer medication; a cholesterol reducing agent; an opioid such as morphine; or an anti-osteoporotic such as raloxifene or alendronate.

The term Apeptide@ as used herein is intended to be broadly construed as inclusive of polypeptides per se having molecular weights of up to 10,000. As used herein, the term Acovalently coupled@ means that the specified moieties are either directly covalently bonded to one another, or else are indirectly covalently joined to one another through an intervening moiety or moieties, such as a bridge, spacer, or linage moiety or moieties. The term Aconjugatively coupled@ means that the specified moieties are covalently coupled to one another. The term Atherapeutic agent@ means an agent which is therapeutically useful, e.g., an agent for the prevention, treatment, remission or attenuation of a disease state, physiological condition, symptoms, or etiological factors, or for the evaluation or diagnosis thereof.

The invention thus comprehends various compositions for therapeutic (in vivo) application, wherein the therapeutic agent of the therapeutic agent composition is a physiologically active, or bioactive, therapeutic agent. In such therapeutic agent-containing compositions, the conjugation of the therapeutic agent component to the oligo(ethylene glycol)-terminated dithiolane component may be direct covalent bonding or indirect (through appropriate spacer groups) bonding. Thus, a wide variety of therapeutic agent species may be accommodated in the broad practice of the present invention, as necessary or desirable in a given end use therapeutic application.

In another aspect, therapeutic agent compositions such as those described above may utilize therapeutic agent components intended for diagnostic or in vitro applications, wherein the therapeutic agent is, for example, a diagnostic reagent or a complement of a diagnostic conjugate for immunoassay or other diagnostic or non-in vivo applications. In such non-therapeutic applications, the compositions of the invention are highly usefully employed as stabilized compositions which may, for example, be formulated in compatible solvents or other solution-based compositions to provide stable compositional forms which are of enhanced resistance to degradation.

Also provided in accordance with the invention is a self-assembled monolayer (SAM) composition comprising an activated or reactive, OEG-modified-1,2-dithiolane composition or a conjugate of an OEG-modified-1,2-dithiolane composition adherent to gold, silver, copper, mercury, or an amalgam of these metals. A SAM composition comprising an activated or reactive, OEG-modified-1,2-dithiolane composition or a conjugate of an OEG-modified-1,2-dithiolane composition adherent to gold is most preferred. Further provided are methods for the preparation of these self-assembled monolayers and methods for their dissociation.

The unexpected utility of an activated or reactive, oligo(ethylene glycol)-terminated 1,2-dithiolane composition of the present invention or a conjugate of a reactive, OEG-terminated 1,2-dithiolane composition of the present invention as compared to the utility of the linear OEG-terminated, linear alkyl monothiols known in the art is believed to come from five sources. First, the 1,2-dithiolane segment of a 1,2-dithiolane composition of the present invention reacts with gold or another metal of the present invention to provide a self-assembled monolayer (SAM) composition that is stabilized by multiple sulfur-metal bonds. The multiple sulfur-metal bonds render the resulting SAM composition more stable than that of a monothiol. Second, the other segment of a 1,2-dithiolane composition of the present invention presents at least one activated or reactive terminus available for binding a biological or non-biological receptor, ligand, sequestering, or reporter moiety, or presents at least one terminus to which a biological or non-biological receptor, ligand, sequestering, or reporter moiety may be bound covalently. Third, when bound to the metal surface, a 1,2-dithiolane composition of the present invention is chemically stable in a wide variety of hostile media and conditions. This stability enables presentation of at least one biological or non-biological receptor, ligand or reporter moiety and capture and/or extraction and/or sequestering of a species of interest from a complex environment without undesirable dissociation of the oligo(ethylene glycol)-terminated dithiolane-metal complex during exposure to the hostile environment. Fourth, each of the opposing termini at the end of the OEG-portion of a 1,2-dithiolane composition of the present invention is reactive with, or may be activated to be reactive with, any one of a broad spectrum of electrophilic or nucleophilic reagents. This reactivity enables covalent attachment of a biological or non-biological receptor, ligand, sequestering, or reporter moiety to an activated or reactive, oligo(ethylene glycol)-terminated 1,2-dithiolane composition of the present invention either prior to its attachment to a metal or following its attachment to a metal. Further, if the OEG-portion of a 1,2-dithiolane composition of the present invention is branched, each activated or reactive terminus of an OEG-branch may be joined covalently to a biological or non-biological receptor, ligand or reporter moiety, thereby enabling presentation of a plurality of ligand or reporter moieties. Presentation of a plurality of a biological or non-biological receptor, ligand or reporter moieties is believed to enable more effective binding of a species of interest and its sequestration from a complex environment. Fifth, each composition of the present invention presents a moderately hydrophilic surface (i.e., the OEG-portion of a composition of the present invention) to the external environment. Monolayers of poly- or oligo(ethylene glycol) derivatives are known to minimize non-specific binding of biomolecules to the interactive terminus of the SAM. (C. Pale-Grosdemange, E. S. Simon, K. L. Prime, and G. M. Whitesides. Formation of self-assembled monolayers by chemisorption of derivatives of oligo(ethylene glycol) of structure $HS(CH_2)11(OCH_2CH_2)_m$ OH on gold. J. Am. Chem. Soc. 1991; 113: 12–20.)

In addition to the five utilities cited above, a sixth utility has not been heretofore recognized by skilled artisans and applies particularly to the 1,2-dithiolane compositions of the present invention. Application of electrical voltage to a gold-sulfur-terminated reagent complex is known to effect the severance of the gold-sulfur reagent bond and release the reagent as a thiol. With respect to an OEG-terminated 1,2-dithiolane composition of the present invention, application of voltage to a gold-complex of a 1,2-dithiolane composition of the present invention severs both gold-sulfur bonds and releases the composition as the dithiol. Surprisingly, the inventor has found that this dithiol rapidly oxidizes to a ring-closed disulfide (i.e., a 1,2-dithiolane of the present invention).

This unexpected and rapid ring closure to a 1,2-dithiolane composition of the present invention offers distinct advantages to users of the present invention. One significant advantage relates to the relative nucleophilicity and reactivity of thiols compared to the nucleophilicity and reactivity of disulfides. Thiols are nucleophiles, and can undergo a variety of reactions, including, for example, the displacement of another thiol that is part of a disulfide. Thus, release of a thiol enables undesirable displacement reactions to occur, reactions that destroy (i.e., "scramble") existing disulfide bonds that may be critical to the structure and activity of a protein and cause its inactivation or denaturation. (Insulin is an example of a protein in which maintenance of the native disulfide bonds is critical. If insulin is exposed to a thiol, "scrambling" of the internal disulfide bonds takes place, and the protein is inactivated.) In contrast, after release from a SAM composition of the present invention, a 1,2-dithiolane of the present invention is re-formed. The disulfide (i.e., 1,2-dithiolane) thus formed is not a nucleophile and does not cause displacement reactions. The lack of chemical reactivity of the 1,2-dithiolane segment of a 1,2-dithiolane of the present invention is advantageous to the user of the present invention in a number of ways, including, by way of example, enabling monitoring of a 1,2-dithiolane composition of the present invention by surface plasmon resonance or mass spectrometry.

A seventh advantage of the 1,2-dithiolanes of the present invention relates specifically to the embodiments in which the 1,2-dithiolane is thioctic acid, d-thioctic acid or a derivative thereof, d-Thioctic acid is a natural substance found in mammals and is an important biological anti-oxidant and enzyme co-factor. Since some of the 1,2-dithiolanes of the present invention are derivatives of d-thioctic acid, it is reasonable to anticipate that these dithiolanes will be physiologically compatible. This is advantageous to the user of the present invention in a number of ways, including, by way of example, enabling use of such a 1,2-dithiolane of the present invention as a means for drug delivery.

The oral route of administration of peptides and proteins is among the most problematic of delivery regimens. Drug delivery via the gastrointestinal (GI) tract requires relatively lengthy exposure to a multi-faceted system that is designed to degrade nutrients and dietary materials into small molecules that are readily transferred from the GI tract into the systemic circulation and to prevent the indiscriminate passage of macromolecules, as well as other large entities such as microbes that may present dangers to the host.

Designing and formulating a polypeptide drug for delivery through the GI tract requires a multitude of strategies. The dosage form must initially stabilize the drug while making it easy to take orally. It must then protect the polypeptide from the extreme acidity and action of pepsin in the stomach. When the drug reaches the intestine, the formulation must incorporate some means for limiting drug degradation by the plethora of enzymes that are present in the intestinal lumen. In addition, the polypeptide and/or its formulations must facilitate both aqueous solubility at near neutral pH and lipid layer penetration in order for the protein to traverse the intestinal membrane and then the basal membrane for entry into the bloodstream. To accomplish this, formulation excipients that promote absorption may be required. Finally, when the modified polypeptide enters the systemic circulation, the structural modifications may add to the functionality of the drug, e.g., by extending its half-life in the circulation. However, any structural changes that may have been employed to enhance oral bioavailability must not interfere with receptor binding and uptake at the site of biological activity.

Therefore, a physiologically active therapeutic agent composition comprising a physiologically active therapeutic agent covalently coupled to a physiologically compatible oligo(ethylene glycol)-modified 1,2-dithiolane moiety wherein the physiologically active therapeutic agent is a peptide or protein and the composition has the ability to interact with biological membranes is a particularly advantageous embodiment of the present invention.

Other aspects, features, and modifications of the invention will be more fully apparent from the ensuing disclosure and appended claims.

DETAILED DESCRIPTION OF THE INVENTION

EXAMPLE 1

Figure 1:
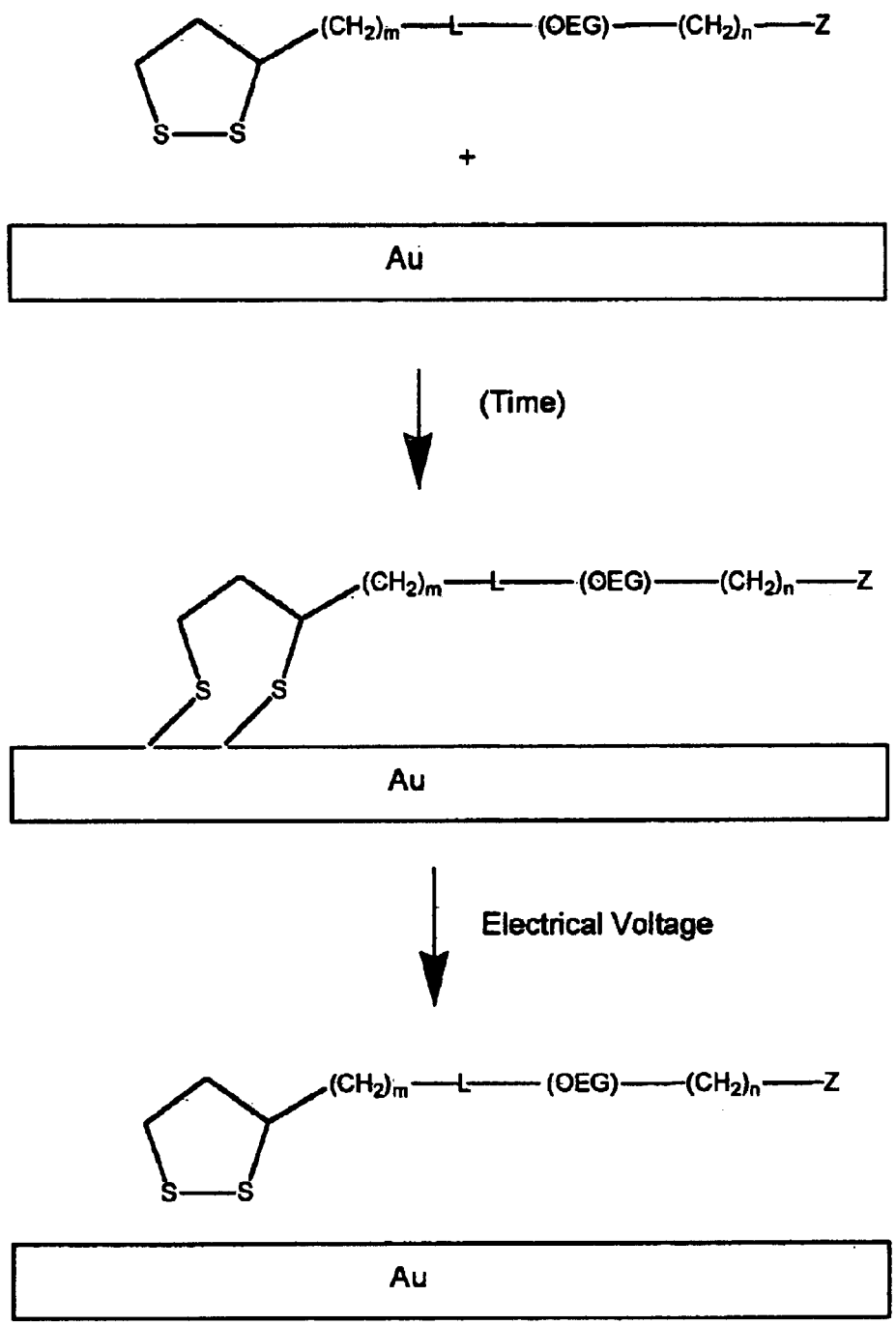
FIG. 1 is a cartoon of the manner in which a 1,2-dithiolane composition of the present invention reacts with a metal surface (e.g., gold) to provide a self-assembled monolayer (SAM) composition of the present invention and subse-

General Procedure for Coupling Thioctic Acid and an OEG-Amine.

To a solution of thioctic acid (0.15 mmol) in methylene chloride (4 mL) at 0° C. is added an OEG-amine (0.23 mmol), N-hydroxybenzotriazole (0.23 mmol) and finally N-(3-dimethylaminoproopyl)-N'-ethylcarbodiimide (EDC) (0.23 mmol). The reaction mixture is allowed to attain room temperature. After 12 h, it is diluted with methylene chloride (10 mL) and washed with 0.1 M HCl (10 mL) and water (10 mL). The organic solution is dried over anhydrous magnesium sulfate and evaporated. The crude product is crystallized or purified by flash chromatography (ethyl acetate/hexane or ethyl acetate/methanol).

(a) In this manner, thioctic acid is coupled with an OEG-amine having the general structure $H_2N$—$CH_2CH_2$—$(OCH_2CH_2)_x$—NH-t-BOC, where x is 2, 4, 6, 8, 10, and 12. The protecting t-BOC group is removed by treatment with trifluoroacetic acid to provide a reactive, oligo(ethylene glycol)-terminated thioctamide suitable for coupling (i.e., conjugating) with a biological or non-biological receptor, ligand or reporter moiety.

(b) Likewise, in this manner, thioctic acid is coupled with an OEG-amine having the general structure $H_2N$—$CH_2CH_2$—$(OCH_2CH_2)_x$—$CO_2H$, where x is 2, 4, 6, 8, 10, and 12, to provide a reactive, oligo(ethylene glycol)-terminated thioctamide suitable for coupling with a biological or non-biological receptor, ligand or reporter moiety.

(c) Likewise, in this manner, thioctic acid is coupled with an OEG-amine having the general structure $H_2N$—$CH_2CH_2$—$(OCH_2CH_2)_x$—OH, where x is 2, 4, 6, 8, 10, and 12, to provide a reactive, oligo(ethylene glycol)-terminated thioctamide suitable for coupling with a biological or non-biological receptor, ligand or reporter moiety.

(d) Thioctic acid is allowed to react with disuccinimidyl carbonate in methylene chloride solution containing triethylamine to provide N-oxysuccinimidyl thioctate (NHS-thioctate), an activated ester of thioctic acid. Then NHS-thioctate is allowed to react with one equivalent of an OEG-hydrazine having the general structure $H_2N$—NH—$CH_2CH_2$—$(OCH_2CH_2)_x$—NH-t-BOC, where x is 2, 4, 6, 8, 10, and 12. The protecting t-BOC group is removed by treatment with trifluoroacetic acid to provide a reactive, oligo(ethylene glycol)-terminated thioctyl hydrazide suitable for coupling with a biological or non-biological receptor, ligand or reporter moiety.

EXAMPLE 2

General Procedure for Coupling d- or l-Thioctic Acid and an OEG-Amine.

Racemic thioctic acid is resolved into its d- and l-isomers.

(a) Using the general procedure described in Example 1, d-thioctic acid is coupled with an OEG-amine having the general structure $H_2N$—$CH_2CH_2$—$(OCH_2CH_2)_x$—NH-t-BOC, where x is 2, 4, 6, 8, 10, and 12. The protecting t-BOC group is removed by treatment with trifluoroacetic acid to provide a reactive, linear oligo(ethylene glycol)-terminated d-thioctamide suitable for coupling with a biological or non-biological receptor, ligand or reporter moiety.

(b) Likewise, in this manner, d-thioctic acid is coupled with an OEG-amine having the general structure $H_2N$—$CH_2CH_2$—$(OCH_2CH_2)_x$—$CO_2H$, where x is 2, 4, 6, 8, 10, and 12, to provide a reactive, oligo(ethylene glycol)-terminated d-thioctamide suitable for coupling with a biological or non-biological receptor, ligand or reporter moiety.

(c) Using the general procedure described in Example 1, d-thioctic acid is coupled with an OEG-amine having the general structure $H_2N$—$CH_2CH_2$—$(OCH_2CH_2)_x$—OH, where x is 2, 4, 6, 8, 10, and 12, to provide a reactive, oligo(ethylene glycol)-terminated d-thioctamide suitable for coupling with a biological or non-biological receptor, ligand or reporter moiety.

(d) Using the general procedure described in Example 1, l-thioctic acid is coupled with an OEG-amine having the general structure $H_2N$—$CH_2CH_2$—$(OCH_2CH_2)_x$—NH-t-BOC, where x is 2, 4, 6, 8, 10, and 12. The protecting t-BOC group is removed by treatment with trifluoroacetic acid to provide a reactive, oligo(ethylene glycol)-terminated l-thioctamide suitable for coupling with a biological or non-biological receptor, ligand or reporter moiety.

(e) Likewise, in this manner, l-thioctic acid is coupled with an OEG-amine having the general structure $H_2N$—$CH_2CH_2(OCH_2CH_2)_x$—$CO_2H$, where x is 2, 4, 6, 8, 10, and 12, to provide a reactive, oligo(ethylene glycol)-terminated l-thioctamide suitable for coupling with a biological or non-biological receptor, ligand or reporter moiety.

(f) Likewise, in this manner, l-thioctic acid is coupled with an OEG-amine having the general structure $H_2N$—$CH_2CH_2$—$(OCH_2CH_2)_x$—OH, where x is 2, 4, 6, 8, 10, and 12, to provide a reactive, oligo(ethylene glycol)-terminated l-thioctamide suitable for coupling with a biological or non-biological receptor, ligand or reporter moiety.

EXAMPLE 3

General Procedure for Coupling Thioctyl Hydrazide and an OEG-Aldehyde.

To a solution of thioctyl hydrazide (0.15 mmol) in ethanol (5 mL) at 0° C. is added OEG-aldehyde (0.23 mmol) and sodium cyanoborohydride (0.5 mmol). The reaction mixture is stirred until thin-layer chromatographic analysis of an aliquot of the reaction mixture indicates that Schiff-base formation and reduction to the secondary amine are complete. The product is isolated by the addition of cold diethyl ether, washed with fresh ether, and purified by flash chromatography on silica gel.

EXAMPLE 4

General Procedure for Coupling Thioctyl Hydrazide and an OEG-Mesylate.

To a solution of thioctyl hydrazide (0.15 mmol) in ethanol (5 mL) at 0° C. is added OEG-Mesylate (0.23 mmol). The reaction mixture is stirred with gentle warming until thin-layer chromatographic analysis of an aliquot of the reaction mixture indicates that alkylation is complete. The product is isolated by the addition of cold diethyl ether, washed with fresh ether and purified by flash chromatography on silica gel.

EXAMPLE 5

General Method for the Preparation of a SAM Composition on Gold.

(a) A 1 mM solution of an OEG-terminated 1,2-dithiolane composition of the present invention is prepared in deoxygenated, absolute alcohol, and a gold surface is placed in contact with the solution for 24 hours at room temperature.

In the case of a conjugate of a 1,2-dithiolane of the present invention, it is preferred that the conjugate be prepared prior preparation of a SAM composition. This is accomplished by reacting a reactive or activated, OEG-terminated 1,2-dithiolane of the present invention with a biological or non-biological receptor, ligand, sequestering, or reporter moiety such as a polypeptide, protein, enzyme, phospholipid, lipid, liposome, nucleoside, oligonucleotide, drug, dye, antibody, reporter molecule, ligand, cyclodextrin, carceplex, boronate, biological membrane, or a surface of a solid material that is compatible with living organisms, tissue, or fluids. Alternatively, a biological or non-biological receptor, ligand, sequestering, or reporter moiety such as a polypeptide, protein, enzyme, phospholipid, lipid, liposome, nucleoside, or oligonucleotide; drug, dye, antibody, reporter molecule, ligand, cyclodextrin, carceplex, boronate, biological membrane, or a surface of a solid material that is compatible with living organisms, tissue, or fluids is covalently bound to a reactive or activated, OEG-terminated SAM composition of the present invention.

(b) A gold surface is exposed to a 50 mM solution of an OEG-terminated 1,2-dithiolane composition in 100 mM phosphate buffer, pH 7.4, at room temperature. Adsorption is achieved at open circuit or at an applied potential.

In the case of a conjugate of a 1,2-dithiolane composition of the present invention, it is preferred that the conjugate be prepared prior preparation of a SAM composition. This is accomplished by reacting a reactive or activated, OEG-terminated 1,2-dithiolane composition of the present invention with a biological or non-biological receptor, ligand, sequestering, or reporter moiety such as a polypeptide, protein, enzyme, phospholipid, lipid, liposome, nucleoside, oligonucleotide, drug, dye, antibody, reporter molecule, ligand, cyclodextrin, carceplex, biological membrane, or a surface of a solid material that is compatible with living organisms, tissue, or fluids. Alternatively, a biological or non-biological receptor, ligand, sequestering, or reporter moiety such as a polypeptide, protein, enzyme, phospholipid, lipid, liposome, nucleoside, or oligonucleotide; drug, dye, antibody, reporter molecule, ligand, cyclodextrin, carceplex, biological membrane, or a surface of a solid material that is compatible with living organisms, tissue, or fluids is covalently bound to the OEG-terminated SAM composition.

EXAMPLE 6

General Method for the Removal of a SAM Composition on Gold.

A SAM composition of the present invention is removed from the gold in 100 mM phosphate buffer, pH 7.4, by application of potential pulses for about 15 minutes in a buffer flow of about 0.5 mL/min.

EXAMPLE 7

Conjugation of a Carboxyl-OEG-Terminated 1.2-Dithiolane with an Enzyme.

A carboxyl-OEG-terminated thioctamide (x is 8) is prepared as described in Example 1 (b). The terminal carboxyl group of the OEG portion of the composition is converted to an activated, N-hydroxysuccinimidyl (NHS) ester by treatment with disuccinimidyl carbonate in methylene chloride solution to provide an activated ester of the OEG-terminated thioctamide. A solution of horseradish peroxidase (HRP) is prepared in 5 mM phosphate buffer, pH 7.0, at a concentration of about 1 mg/mL. An equimolar volume of the HRP solution is added to the NHS-ester of the OEG-terminated thioctamide and the resulting mixture is allowed to stir for 24 hours at 4° C.

EXAMPLE 8

Conjugation of a Hydroxy-OEG-Terminated 1.2-Dithiolane with an Oligonucleotide Probe.

Thioctic acid is coupled with an OEG-amine having the structure $H_2N-CH_2CH_2-(OCH_2CH_2)_{10}-OH$ to provide a reactive oligo(ethylene glycol)-terminated thioctamide, thioctamide-$CH_2CH_2-(OCH_2CH_2)_{10}-OH$. This thioctamide is coupled with a phosphoramidite-protected oligo-dT sequence using standard phosphoramidite chemistry, and the product is hydrolyzed to provide thioctamide-$CH_2CH_2-(OCH_2CH_2)_{10}$—O-oligo-dT.

(b) Preparation of the thioctamide-$CH_2CH_2-(OCH_2CH_2)_{10}$—O-oligo-dT SAM. A gold surface is prepared. The surface is exposed to a phosphate buffer solution of the thioctamide-$CH_2CH_2-(OCH_2CH_2)_{10}$—O-oligo-dT composition for 4 hours. Ellipsometric measurements result in values that are in good agreement with those expected for a well-packed SAM containing trans-extended alkanethiolates.

It is known that oligo-dT chains bind with the poly-A tails present on most mRNA sequences. Therefore, it is reasonable to anticipate that the oligo-dT-terminated SAM composition of the present invention will be useful for the isolation of mRNAs from complex media. Durst and colleagues (R. Durst et al. Analyt. Chem. 2001; 73: 3162–3167) have recently shown that the expression of mRNA can be used to distinguish living cells from dead ones.

EXAMPLE 9

(a) Conjugation of a Carboxyl-OEG-terminated 1,2-Dithiolane with a Polypeptide.

A carboxyl-OEG-terminated thioctamide (x is 8) is prepared as described in Example 1 (b). The bis(1,1-dimethylethyl)ester of N-[(phenylmethoxy)carbonyl)glycyl-$N^5$-[[[(3,4-dihydro-2,2,5,7,8-pentamethyl-2H-1-benzopyran-6-yl)sulfonyl]amino]iminomethyl]-L-ornithylglycyl-L-aspartic acid (a protected RGD tripeptide) is prepared using the method of Roberts et al. (C. Roberts, C. S. Chen, M. Mrksich, V. Martichonok, D. E. Ingber, and G. M. Whitesides. J. Am. Chem. Soc. 1998; 120: 6548–6555.) The protecting phenylmethoxycarbonyl group is removed by hydrogenation over 10% Pd/C; the catalyst is removed by filtration and the crude amine is concentrated in vacuo. Equimolar quantities of the amine and the carboxyl-OEG-terminated thioctamide are combined, the flask is purged with nitrogen, dry DMF is added, and the stirred solution is cooled to 0° C. An excess of diphenylphosphoryl azide is added, followed by a solution of di-isopropyl ethylamine in DMF, and stirring at 0° C. is continued for 10 hours. The mixture is diluted with ethyl acetate and washed successively with water, 5% aqueous sodium bicarbonate, and brine. The organic phase is dried, and the solvent is removed in vacuo to give a residue that is chromatographed to give product. The remaining protective groups are removed by exposing a methylene chloride solution of the product to trifluoroacetic acid. Repeated precipitation of the product from methylene chloride using diethyl ether is used to purify the desired product, thioctamide-OEG-C(O)NH-GRGD-OH.

(b) Preparation of the thioctamide-OEG-C(O)NH-GRGD-OH SAM. A gold surface is prepared. The surface is exposed to a phosphate buffer solution of the thioctamide-OEG-C(O)NH-GRGD-OH composition for 4 hours. Ellipsometric measurements result in values that are in good agreement with those expected for a well-packed SAM containing trans-extended alkanethiolates.

(c) Cell Attachment to the SAM. The tripeptide arginine-glycine-aspartate (RGD) promotes cell adhesion by binding to cell surface integrin receptors. Bovine capillary endothelial cells are isolated from adrenal cortex and cultured. Cells are dissociated with trypsin-EDTA, washed with Dulbecco's Modified Eagle Medium containing 1% bovine serum albumin, and plated onto substrates in chemically defined media before incubation in 10% CO2 at 37° C. A fixed number of cells are plated onto substrates containing the thioctamide-OEG-C(O)NH-GRGD-OH-SAM composition. After 4 hours, substrates are gently washed in PBS and fixed with 4% paraformaldehyde in PBS for 30 min. The number of cells attached per field is determined from photographs taken of samples on a microscope at 200× magnification.

Alternatively, after incubation times ranging from 4 to 24 hours, the immobilized cells are not fixed with paraformaldehyde but are removed using two techniques. In some experiments, the SAM-bound cells are exposed to a solution containing soluble GRGDSP, a polypeptide that will detach the cells. In other experiments, a voltage is applied to the gold surface, and the gold-thiol bonds are severed, freeing the thioactamide-labeled cells.

EXAMPLE 10

Conjugation of an Amino-OEG-Terminated 1.2-Dithiolane with a Sugar Phosphonate.

(a) Thioctic acid is coupled with an OEG-amine having the structure $H_2N$—$CH_2CH_2$—$(OCH_2CH_2)_x$—OH, where x is 10, to provide a reactive, oligo(ethylene glycol)-terminated thioctamide, thioctamide-$CH_2CH_2$—$(OCH_2CH_2)_{10}$—OH. This thioctamide is coupled with a protected mannose-6-phosphonate using standard phosphoramidite chemistry. Likewise, the oligo(ethylene glycol)-terminated thioctamide is coupled with a protected mannose-6-difluoromethylphosphonate using standard phosphoramidite chemistry. The protective groups are removed from each compound to provide thioctamide-$CH_2CH_2$—$(OCH_2CH_2)_{10}$—O-(6-methylphosphono) mannose and thioctamide-$CH_2CH_2$—$(OCH_2CH_2)_{10}$—O-(6-difluoromethylphosphono)mannose, respectively.

(b) Preparation of the thioctamide-$CH_2CH_2$—$(OCH_2CH_2)_{10}$—O-(6-methylphosphono)mannose SAM. A gold surface is prepared. The surface is exposed to a phosphate buffer solution of the thioctamide-$CH_2CH_2$—$(OCH_2CH_2)_{10}$—O-(6-phosphonomethyl)mannose composition for 4 hours. Ellipsometric measurements result in values that are in good agreement with those expected for a well-packed SAM containing trans-extended alkanethiolates.

(c) Cell Attachment to the SAM. The population of mannose-6-phosphate receptors is increased abnormally in breast cancer cells. Since mannose-6-phosphate is readily hydrolyzed, it is not useful as a ligand for selective extraction of cancer cells from media containing a variety of cell types. In contrast, mannose-6-phosphonate and mannose-6-difluoromethylphosphonate are stable to hydrolysis and retain the ability to bind to mannose-6-phosphate receptors.

The phosphonomannose-terminated SAM prepared as described in Example 10(b) is exposed to a serum sample containing breast cancer cells. After 4 hours, substrates are gently washed in PBS and fixed with 4% paraformaldehyde in PBS for 30 min. The number of cells attached per field is determined from photographs taken of samples on a microscope at 200× magnification. The number of cells attached per field demonstrates the utility of the SAM for selective extraction of cancer cells from complex environments.

EXAMPLE 11

Conjugation of a Hydroxyl-OEG-Terminated 1,2-Dithiolane with a Drug (5-Aminosalicylic Acid).

Thioctic acid is coupled with an OEG-amine having the structure $H_2N$—$CH_2CH_2$—$(OCH_2CH_2)_{10}$—OH to provide a reactive oligo(ethylene glycol)-terminated thioctamide, thioctamide-$CH_2CH_2$—$(OCH_2CH_2)_{10}$—OH. This product is converted to the mesylate ester by reaction with methanesulfonyl chloride in methylene chloride solution containing triethylamine. The mesylate ester is isolated and purified by flash chromatography on silica gel.

5-Aminosalicylic acid is a drug used in the treatment of ulcerative colitis. To a solution containing an excess of 5-aminosalicylic acid hydrochloride and thioctamide-$CH_2CH_2$—$(OCH_2CH_2)_{10}$—O-Ms (the mesylate ester) in DMF is added triethylamine until dissolution of 5-aminosalicylic acid is achieved. The reaction is allowed to stir until thin-layer chromatographic analysis of an aliquot indicates reaction is complete. The 5-aminosalicylate conjugate is isolated and purified by flash chromatography on silica gel.

(b) Preparation of the thioctamide-$CH_2CH_2$—$(OCH_2CH_2)_{10}$-5-aminosalicylate SAM. A gold surface is prepared. The surface is exposed to an ethanol solution of the thioctamide-$CH_2CH_2$—$(OCH_2CH_2)_{10}$-5-aminosalicylate composition for 4 hours. Ellipsometric measurements result in values that are in good agreement with those expected for a well-packed SAM containing trans-extended alkanethiolates.

EXAMPLE 12

Conjugation of a Carboxyl-OEG-Terminated 1,2-Dithiolane with Insulin.

A carboxyl-OEG-terminated thioctamide (x is 8) is prepared as described in Example 1(b). The terminal carboxyl group of the OEG portion of the composition is converted to an activated, N-hydroxysuccinimidyl (NHS) ester by treatment with disuccinimidyl carbonate in methylene chloride solution to provide an activated ester of the OEG-terminated thioctamide. A solution of insulin is prepared in dimethylsulfoxide (DMSO) at a concentration of about 1 mg/mL containing 2–3 mole equivalents of triethylamine. A solution of 2 mole equivalents of the NHS-ester of the OEG-terminated thioctamide in a minimum volume of acetonitrile is added to the insulin solution, and the resulting mixture is allowed to stir for 24 hours at 4° C. Reversed-phase HPLC analysis indicates that conjugation to insulin takes place at lysine-29 on the beta-chain of insulin.

When a 10 mg/mL solution of the OEG-terminated 1,2-dithiolane-conjugated insulin is administered to a mouse by oral gavage of a 10 mL/kg dose, a reduction in the animal's serum glucose is observed. This observation indicates the carboxyl-OEG-terminated 1,2-dithiolane-conjugated insulin is orally bioavailable.

EXAMPLE 13

Conjugation of a Carboxyl-OEG-Terminated 1,2-Dithiolane with Raloxifene.

Raloxifene hydrochloride is a selective estrogen receptor modulator (SERM) that belongs to the benzothiophene class of compounds. The chemical designation is [6-hydroxy-2-(4-hydroixyphenyl)benzo[b]thien-3-yl]-4-[2-(1-piperidinyl) ethoxy]phenyl]methanone hydrochloride and the molecular weight is 510.5. Raloxifene decreases resorption of bone and reduces biochemical markers of bone turnover to the pre-menopausal range. Raloxifene also has beneficial effects on lipid metabolism. Raloxifene decreases total and LDL cholesterol levels but does not increase triglyceride levels. It does not change total HDL cholesterol levels. Clinical trial data indicate that raloxifene lacks estrogen-like effects on the uterus and breast tissue. About 60% of the drug is absorbed rapidly after oral administration, but presystemic glucuronide conjugation is estensive. As a result, absolute bioavailability is reduced to about 2%. Lipoamide-OEG-oligomer conjugates of raloxifene are prepared to study the change in oral bioavailability of the drug and enhance its absolute bioavailability in humans.

A carboxyl-OEG-terminated thioctamide (x is 8) is prepared as described in Example 1(b). The terminal carboxyl group of the OEG portion of the composition is converted to an activated, N-hydroxysuccinimidyl (NHS) ester by treatment with disuccinimidyl carbonate in methylene chloride solution containing triethylamine to provide an activated ester of the OEG-terminated thioctamide. A solution of raloxifene hydrochloride (5 g, 0.01 mol) is prepared by dissolving the solid in acetonitrile (100 mL) containing a 5 mole excess of triethylamine. A concentrated solution of 2.2 mole equivalents of the NHS-ester of the OEG-terminated thioctamide in a minimum volume of acetonitrile is added, and the resulting mixture is allowed to stir for 24 hours at ambient temperatures. Reversed-phase HPLC analysis indicates that conjugation to ranitidine takes place at each of the phenolic hydroxyl groups on the molecule.

EXAMPLE 14

Conjugation of a Hydroxy-OEG-Terminated 1,2-Dithiolane with a Bisphosphonate, a Preferred Embodiment.

Alendronate sodium is a bisphosphonate anti-osteoporotic that acts as a specific inhibitor of osteoclast-mediated bone resorption in both men and women. Bisphosphonates are synthetic analogs of pyrophosphate that bind to the hydroxyapatite found in bone. The chemical name for alendronate sodium is (4-amino-1-hydroxybultylidene) bisphosphonic acid, monosodium salt. Relative to an intravenous reference dose, the mean oral bioavailability of alendronate in women was 0.64% for doses ranging from 5 to 70 mg when administered after an overnight fast and two hours before a standardized breakfast. Oral bioavailability of the 10 mg tablet in men was similar to that in women. Lipoamide-OEG-oligomer conjugates of alendronate are prepared to study the change in oral bioavailability of the drug, enhance its absolute bioavailability, and reduce its adverse effects in humans.

Thioctic acid is coupled with an OEG-amine having the structure $H_2N-CH_2CH_2-(OCH_2CH_2)_{10}-OH$ to provide a reactive oligo(ethylene glycol)-terminated thioctamide, thioctamide-$CH_2CH_2-(OCH_2CH_2)_{10}-OH$. The resulting thioctamide is converted to an omega-bromo-OEG-thioctamide, thioctamide-$CH_2CH_2-(OCH_2CH_2)_{10}-Br$. Five equivalents of the omega-bromo-OEG-thioctamide are allowed to react with a slurry of t-butoxycarbonyl-protected (BOC) alendronate sodium in acetonitrile solution containing 5% TDA-1, a phase-transfer catalyst. The BOC-alendronate tetra-ester that is isolated from this esterification reaction is deprotected by treatment with trifluoroacetic acid. A tetra(thioctamide-OEG) ester of alendronate is thus obtained.

Pharmaceutical compositions comprising a stable, conjugated therapeutic agent composition comprising a physiologically active therapeutic agent covalently coupled to a physiologically compatible oligo(ethylene glycol)-modified 1,2-dithiolane moiety as described above are also provided. Whilst it may be possible for a therapeutic agent composition of the present invention to be administered as the raw chemical, it is preferable to present it as a pharmaceutical composition. According to embodiments of the present invention, a pharmaceutical composition includes one or more of the stable, conjugated therapeutic agent compositions described above, and a pharmaceutically acceptable carrier.

The stable, conjugated therapeutic agent composition comprising a physiologically active therapeutic agent covalently coupled to a physiologically compatible oligo (ethylene glycol)-modified 1,2-dithiolane moiety described above may be formulated for administration in a pharmaceutical carrier in accordance with known techniques. See, e.g., Remington, *The Science and Practice of Pharmacy* ($9^{th}$ Ed. 1995).

In the manufacture of a pharmaceutical composition according to embodiments of the present invention, the stable, conjugated therapeutic agent composition is typically admixed with, inter alia, a pharmaceutically acceptable carrier. The carrier must, of course, be acceptable in the sense of being compatible with any other ingredients in the pharmaceutical composition and should not be deleterious to the patient. The carrier may be a solid or a liquid, or both, and is preferably formulated with the stable, conjugated therapeutic agent composition as a unit-dose formulation. The pharmaceutical compositions may be prepared by any of the well-known techniques of pharmacy, including, but not limited to, admixing the formulation components, optionally including one or more accessory ingredients.

The pharmaceutical compositions according to embodiments of the present invention include those suitable for oral, rectal, topical, inhalation (e.g., via an aerosol), buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces), intraocular, and transdermal administration. The most suitable route in any given case will depend on the nature and severity of the condition being treated and on the nature of the particular stable, conjugated therapeutic agent composition which is being used.

Pharmaceutical compositions suitable for oral administration may be presented in discrete units, such as capsules, cachets, lozenges, or tablets, each containing a predetermined amount of the stable, conjugated therapeutic agent composition; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the stable, conjugated therapeutic agent composition and a suitable carrier (which may contain one or more accessory ingredients as noted above). In general, the pharmaceutical composition according to embodiments of the present invention are prepared by uniformly and intimately admixing the stable, conjugated therapeutic agent composition with a liquid or finely divided solid carrier, or both, and then, if necessary, shaping the resulting mixture. For example, a tablet may be prepared by compressing or molding a powder or granules containing the stable, conjugated therapeutic agent composition, optionally with one or more accessory ingredients. Compressed tablets may be prepared by compressing, in a suitable machine, the stable, conjugated therapeutic agent composition in a free-flowing form, such as a powder or granules optionally mixed with a binder, lubricant, inert diluent, and/or surface active or dispersing agent(s). Molded tablets may be made by molding, in a suitable machine, the powdered compound moistened with an inert liquid binder. The tablets may optionally be coated or scored and may be formulated so as to provide slow or controlled release of the active ingredient therein.

Pharmaceutical compositions suitable for buccal (sublingual) administration include lozenges comprising the stable, conjugated therapeutic agent composition in a flavored base, usually sucrose and acacia or tragacanth; and pastilles comprising the stable, conjugated therapeutic agent composition in an inert base such as gelatin and glycerin or sucrose and acacia.

Pharmaceutical composition according to embodiments of the present invention suitable for parenteral administration comprise sterile, aqueous and non-aqueous injection solutions of the stable, conjugated therapeutic agent composition, which preparations are preferably isotonic with the blood of the intended recipient. These preparations may contain anti-oxidants, buffers, baceriostats, and solutes which render the composition isotonic with the blood of the intended recipient. Aqueous and non-aqueous sterile suspensions may include suspending agents and thickening agents. The compositions may be presented in unit-dose or multi-dose containers, for example, sealed ampoules and vials, and may be stored in a freeze-dried (lyophilized) condition requiring only the addition of the sterile liquid carrier, for example, saline or water for injection, immediately prior to use. Extemporaneous injection solutions and suspensions may be prepared from sterile powders, granules, and tablets of the kind previously described. For example, an injectable, stable, sterile composition comprising a stable, conjugated therapeutic agent composition in a unit dosage form in a sealed container may be provided.

Pharmaceutical compositions suitable for rectal administration are preferably presented as unit-dose suppositories. These may be prepared by admixing the stable, conjugated therapeutic agent composition with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Compositions suitable for transdermal administration may also be delivered by iontophoresis (see, for example, *Pharmaceutical Research* 3(6): 318 (1986)) and typically take the form of an optionally buffered aqueous solution of the stable, conjugated therapeutic agent composition. Suitable formulations comprise citrate or bis-tris buffer (pH 6) or ethanol/water and contain from 0.1 to 0.2 M active ingredient.

It should be understood that in addition to the ingredients particularly mentioned above, the formulations of this invention may include other agents conventional in the art having regard to the type of formulation in question, for example those suitable for oral administration may include flavoring agents.

Preferred unit dosage formulations are those containing an effective dose, as hereinbelow recited, or an appropriate fraction thereof, of the active ingredient.

According to other embodiments of the present invention, methods of treating a patient in need of such treatment include administering to the patient an effective amount of a stable, conjugated therapeutic agent composition comprising a physiologically active therapeutic agent covalently coupled to a physiologically compatible oligo(ethylene glycol)-modified 1,2-dithiolane moiety as described above. The therapeutically effective amount of any stable, conjugated therapeutic agent composition, the use of which is in the scope of the present invention, will vary somewhat from one composition to another, and from patient to patient, and may depend on factors such as the age and condition of the patient and the route of delivery. Such dosages can be determined in accordance with routine pharmacological procedures known to those skilled in the art. As a general proposition, a therapeutically effective dose of stable, conjugated therapeutic agent composition will be the weight of active pharmaceutical ingredient per kg of the patient=s body weight (i.e., mg/kg) that is useful for the prevention, prophylaxis, treatment, remission or attenuation of a disease state, physiological condition, symptoms, or etiological factors, or for the evaluation or diagnosis thereof. The duration of treatment depends on the type of condition being treated and may be for as long as the life of the patient.

The skilled artisan will appreciate that the invention has a number of advantages over the prior art, including the following. First, the availability of the compositions of the present invention enables the skilled artisan to use any of a broad spectrum of known chemistries to attach a specific, biological or non-biological receptor, ligand, sequestering, or reporter moiety of interest to the artisan to an activated or reactive, OEG-terminated 1,2-dithiolane composition of the present invention to provide a conjugate of the OEG-terminated 1,2-dithiolane composition. Second, the resulting conjugate is easily used, either as the pure component or as part of a mixture with other thiols, to prepare a stable, self-assembled monolayer composition of the present invention on gold, silver, copper, mercury, or an amalgam of these metals. Third, after use (e.g., for capture, sequestration, and extraction of a species of interest), dissociation of the SAM composition of the present invention is effected, not through the use of the harsh and non-specific chaotropic agents known in the art, but by the controlled application of electrical voltage to the SAM composition. Fourth, after dissociation, the dithiol that is released from the metal surface nearly instantaneously oxidizes to the ring-closed 1,2-dithiolane, providing a moiety that may be identified and quantitated using instrumental techniques such as surface plasmon resonance or mass spectrometry. Fifth, some embodiments of the 1,2-dithiolane compositions of the present invention are derivatives of a natural substance, d-thioctic acid. It is reasonable to anticipate that these embodiments, together with embodiments of the present invention that are derivatives of thioctic acid, will be compatible with physiological systems and will be useful for drug delivery, among other utilities.

With respect to a stable, conjugated therapeutic agent composition of the present invention, the skilled artisan will appreciate that a stable, covalently conjugated therapeutic agent composition exhibits enhanced pharmaceutical and pharmacological properties as compared to the unmodified therapeutic agent, including, but not restricted to, improved bioavailability, the ability to interact with biological membranes, reduced side effects, enhanced resistance to enzymatic degradation, and so forth.

The invention has been described with respect to several particular examples and embodiments. However, the foregoing examples and descriptions are not intended to limit the invention to the exemplified embodiments. The skilled artisan should recognize that variations can be made within the scope and spirit of the invention as described in the foregoing specification. The invention encompasses all alternatives, modifications, and equivalents that may be included within the true scope and spirit of the invention as defined by the appended claims.

I claim:

1. A physiologically active therapeutic agent composition comprising a therapeutic agent stabilizingly and covalently coupled with one or more molecules of a non-naturally occurring oligo(ethylene glycol)-terminated 3-alkyl-1,2-dithiolane moiety, wherein the 3-alkyl-1,2-dithiolane moiety is d-thioctic acid, the composition is able to interact with biological membranes and the therapeutic agent is active in prophylaxis or treatment of conditions or disease states in a mammalian subject or a cell or tissue from said subject.

2. A composition according to claim 1, wherein the covalently coupled therapeutic agent has an enhanced in vivo resistance to enzymatic degradation, relative to the therapeutic agent alone.

3. A composition according to claim 1, wherein the therapeutic agent is selected from the group consisting of peptides, proteins, nucleosides, nucleotides, antiviral agents, antineoplastic agents, anti-osteoporotic agents, and opioids; and the covalently coupled therapeutic agent has an enhanced in vivo resistance to enzymatic degradation, relative to the therapeutic agent alone.

4. A physiologically active therapeutic agent composition comprising a therapeutic agent stabilizingly and covalently coupled with one or more molecules of a non-naturally occurring linear oligo(ethylene glycol)-terminatd 3-alkyl-1, 2-dithiolane moiety, wherein the 3-alkyl-1 2-dithiolane is d-thioctic acid, and the composition is able to interact with biological membranes.

5. A composition according to claim 4, wherein the therapeutic agent comprises a physiologically active agent selected from the group consisting of peptides, proteins, nucleosides, nucleotides, antiviral agents, antineoplastic agents, anti-osteoporotic agents, and opioids; and the covalently coupled therapeutic agent has an enhanced in vivo resistance to enzymatic modification, relative to the therapeutic agent alone.

6. A stable, aqueously soluble, physiologically active therapeutic agent composition comprising a therapeutic agent stabilizingly and covalently coupled to an oligo (ethylene glycol)-terminated d-thioctic acid moiety, wherein the physiologically active therapeutic agent composition has the ability to interact with biological membranes.

7. A composition according to claim 6, wherein the therapeutic agent is covalently coupled to the oligo(ethylene glycol)-terminated d-thioctic acid moiety by a labile covalent bond, wherein the labile covalent bond is scissionable in vivo by biochemical hydrolysis and/or proteolysis.

8. A pharmaceutical composition suitable for administration to a subject in need thereof comprising a physiologically active therapeutic agent composition and a pharmaceutical carrier, wherein said therapeutic agent composition comprises a physiologically active therapeutic agent covalently coupled to a physiologically compatible oligo (ethylene glycol)-terminated d-thioctic acid moiety, wherein the physiologically active therapeutic agent composition has the ability to interact with biological membranes.

9. A physiologically active therapeutic agent composition comprising a physiologically compatible oligo(ethylene glycol)-terminated 3-alkyl-1,2-dithiolane moiety having the formula:

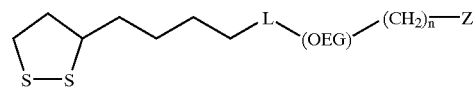

wherein n is from 2 to about 6; the 3-alkyl-1,2-dithiolane moiety is thioctic acid, d-thioctic acid or l-thioctic acid; OEG is a linear oligoether having the general structure $-(OCH_2CH_2)_x-$ and x is from 2 to about 100, or is a branched oligoether wherein each branch comprises a linear oligoether having said general structure; one terminus of the OEG is covalently joined to the alkyl side chain of the 3-alkyl-1,2-dithiolane by a linker L, wherein L is N, O, S, P, an amide or hydrazide; and another terminus of the OEG is stabilizingly and covalently coupled to a physiologically active therapeutic agent Z, wherein the physiologically active therapeutic agent composition has the ability to interact with biological membranes.

10. The composition according to claim 9, wherein the physiologically active therapeutic agent Z is a peptide or protein.

11. The composition according to claim 9, wherein the physiologically active therapeutic agent Z is a peptide selected from the group consisting of insulin, calcitonin, interferon, enkephalin, endorphin, vasopressin, superoxide dismutase, asparaginase, arginase, arginine deaminase, and erythropoietin.

12. The composition according to claim 9, wherein the physiologically active therapeutic agent Z is an anti-resorptive agent.

13. The composition according to claim 9, wherein the physiologically active therapeutic agent Z is a bisphosphonate.

14. A composition according to claim 9, wherein the physiologically active therapeutic agent Z is a selective estrogen receptor modulator.

15. A physiologically active therapeutic agent composition comprising a physiologically compatible oligo(ethylene glycol)-terminated 3-alkyl-1,2-dithiolane moiety having the formula:

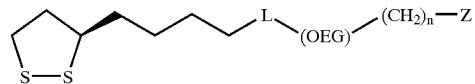

wherein n is from 2 to about 6; the 3-alkyl-1,2-dithiolane is d-thioctic acid; OEG is a linear oligoether having the general structure $-(OCH_2CH_2)_x-$ and x is from 2 to about 100, or is a branched oligoether wherein each branch comprises a linear oligoether having said general structure; one terminus of the OEG is covalently joined to the alkyl side chain of the 3-alkyl-1,2dithiolane by a linker L, wherein L is N, O, S, P, an amide or hydrazide; and another terminus of the OEG is covalently coupled to a therapeutic agent Z selected from the group consisting of alendronate, ritidronate, etidronate, and raloxifene, wherein the physiologically active therapeutic agent composition has the ability to interact with biological membranes.

16. A physiologically active therapeutic agent composition comprising a physiologically compatible oligo(ethylene glycol)-terminated 3-alkyl-1,2-dithiolane moiety having the formula:

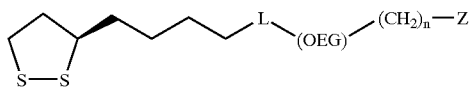

wherein n is from 2 to about 6; the 3alkyl-1,2-dithiolane is d-thioctic acid; OEG is a linear oligoether having the general structure —(OCH$_2$CH$_2$)$_x$— and x is from 2 to about 100, or is a branched oligoether wherein each branch comprises a linear oligoether having said general structure; one terminus of the OEG is covalently joined to the alkyl side chain of the 3-alkyl-1,2-dithiolane by a linker L, wherein L is N, O, S, P, an amide or hydrazide; and another terminus of the OEG is covalently coupled to a physiologically active therapeutic agent Z, wherein said therapeutic agent is insulin, interferon, erythropoietin, or calcitonin, wherein the physiologically active therapeutic agent composition has the ability to interact with biological membranes.

17. A method of prophylactically or interventionally treating a potential or developed condition or disease state in a human or non-human mammalian subject with a therapeutic agent effective for treating said condition or disease, comprising administering to the subject an amount effective for said treating of a stable physiologically active therapeutic agent composition comprising a therapeutic agent covalently coupled to an oligo(ethylene glycol)-terminated d-thioctic acid moiety, wherein the physiologically active therapeutic agent composition has the ability to interact with biological membranes.

* * * * *